(12) United States Patent
Ehrlich

(10) Patent No.: US 10,905,375 B1
(45) Date of Patent: Feb. 2, 2021

(54) FINGERNAIL PULSE MONITOR SYSTEM

(71) Applicant: Kenneth Ehrlich, Borger, TX (US)

(72) Inventor: Kenneth Ehrlich, Borger, TX (US)

(*) Notice: Subject to any disclaimer, the term of this patent is extended or adjusted under 35 U.S.C. 154(b) by 0 days.

(21) Appl. No.: 16/698,814

(22) Filed: Nov. 27, 2019

(51) Int. Cl.
*A61B 5/1455* (2006.01)
*A61B 5/00* (2006.01)
*A61B 5/024* (2006.01)

(52) U.S. Cl.
CPC ........ *A61B 5/6826* (2013.01); *A61B 5/02427* (2013.01); *A61B 5/02438* (2013.01); *A61B 5/14552* (2013.01); *A61B 5/6838* (2013.01); *A61B 2562/0238* (2013.01)

(58) Field of Classification Search
CPC . A61B 5/1455; A61B 5/14552; A61B 5/6826; A61B 5/6832; A61B 2560/0443; A61B 2562/227
See application file for complete search history.

(56) References Cited

U.S. PATENT DOCUMENTS

| | | | |
|---|---|---|---|
| 3,742,635 A | 7/1973 | Hutto | |
| 5,281,792 A | 1/1994 | Lee et al. | |
| 5,879,373 A * | 3/1999 | Roper | A61B 5/14552 600/322 |
| 7,245,953 B1 * | 7/2007 | Parker | A61B 5/14552 600/310 |
| 8,233,955 B2 * | 7/2012 | Al-Ali | A61B 5/6838 600/344 |
| 8,989,831 B2 * | 3/2015 | Al-Ali | A61B 5/14552 600/323 |

* cited by examiner

*Primary Examiner* — Eric F Winakur
(74) *Attorney, Agent, or Firm* — Shannon Warren

(57) ABSTRACT

A monitor system configured to selectively attach a light emitter assembly and a light receiver assembly to a finger. The monitor system comprising the light emitter assembly, the light receiver assembly, an upper assembly a lower assembly, and an intermediate support. The monitor system comprises an attached portion and a detached portion. The attached portion is configured to attach to a fingernail of the finger. The detached portion is configured to selectively and releasably attach to the attached portion. The monitor system is configured to emit one or more emitted lights through the finger between the light emitter assembly and the light receiver assembly.

13 Claims, 16 Drawing Sheets

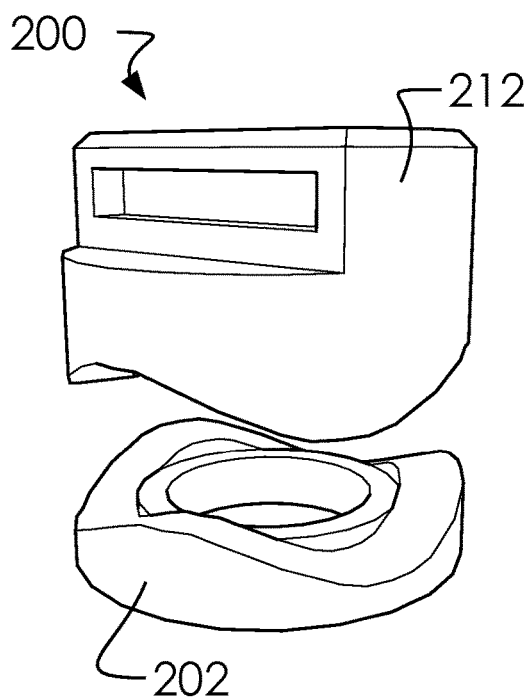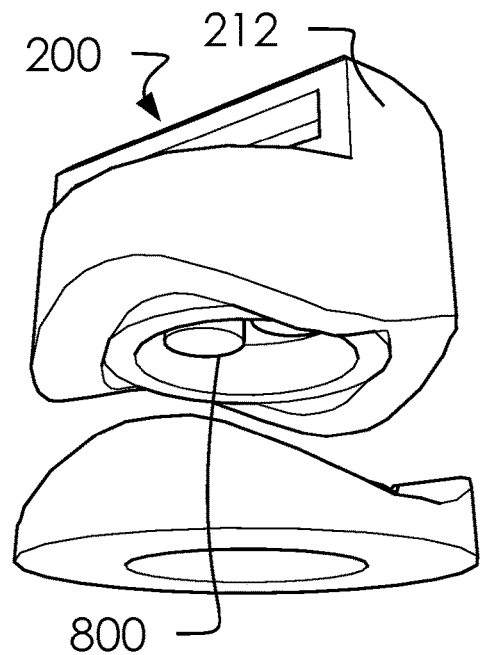
FIG. 8A  FIG. 8B
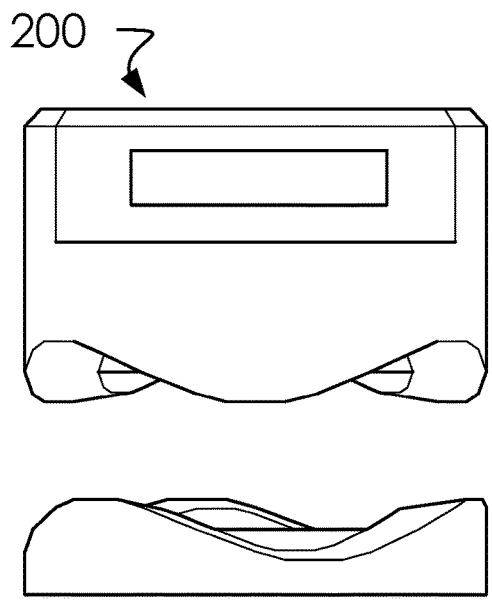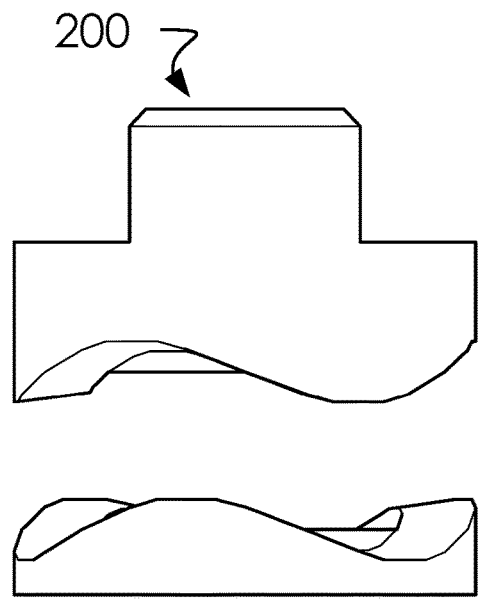
FIG. 8C  FIG. 8D

FINGERNAIL PULSE MONITOR SYSTEM

CROSS-REFERENCE TO RELATED APPLICATIONS

This application claims benefit to U.S. Provisional Patent Application No. 62/772,075, filed Nov. 27, 2018.

STATEMENT REGARDING FEDERALLY SPONSORED RESEARCH OR DEVELOPMENT (IF APPLICABLE)

Not applicable.

REFERENCE TO SEQUENCE LISTING, A TABLE, OR A COMPUTER PROGRAM LISTING COMPACT DISC APPENDIX (IF APPLICABLE)

Not applicable.

BACKGROUND OF THE INVENTION

Prior art known to the Applicant includes U.S. Pat. Nos. 5,281,792A, and 3,742,635A.

None of the known inventions and patents, taken either singularly or in combination, is seen to describe the instant disclosure as claimed.

BRIEF SUMMARY OF THE INVENTION

A monitor system configured to selectively attach a light emitter assembly and a light receiver assembly to a finger. Said monitor system comprising said light emitter assembly, said light receiver assembly, an upper assembly a lower assembly, and an intermediate support. Said monitor system comprises an attached portion and a detached portion. Said attached portion is configured to attach to a fingernail of said finger. Said detached portion is configured to selectively and releasably attach to said attached portion. Said monitor system is configured to emit one or more emitted lights through said finger between said light emitter assembly and said light receiver assembly.

BRIEF DESCRIPTION OF THE SEVERAL VIEWS OF THE DRAWING

FIGS. 8A, 8B, 8C and 8D illustrate an exploded perspective front side view, a perspective bottom side view, an elevated front side view, and an elevated first side view of an upper assembly 200.

DETAILED DESCRIPTION OF THE INVENTION

The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
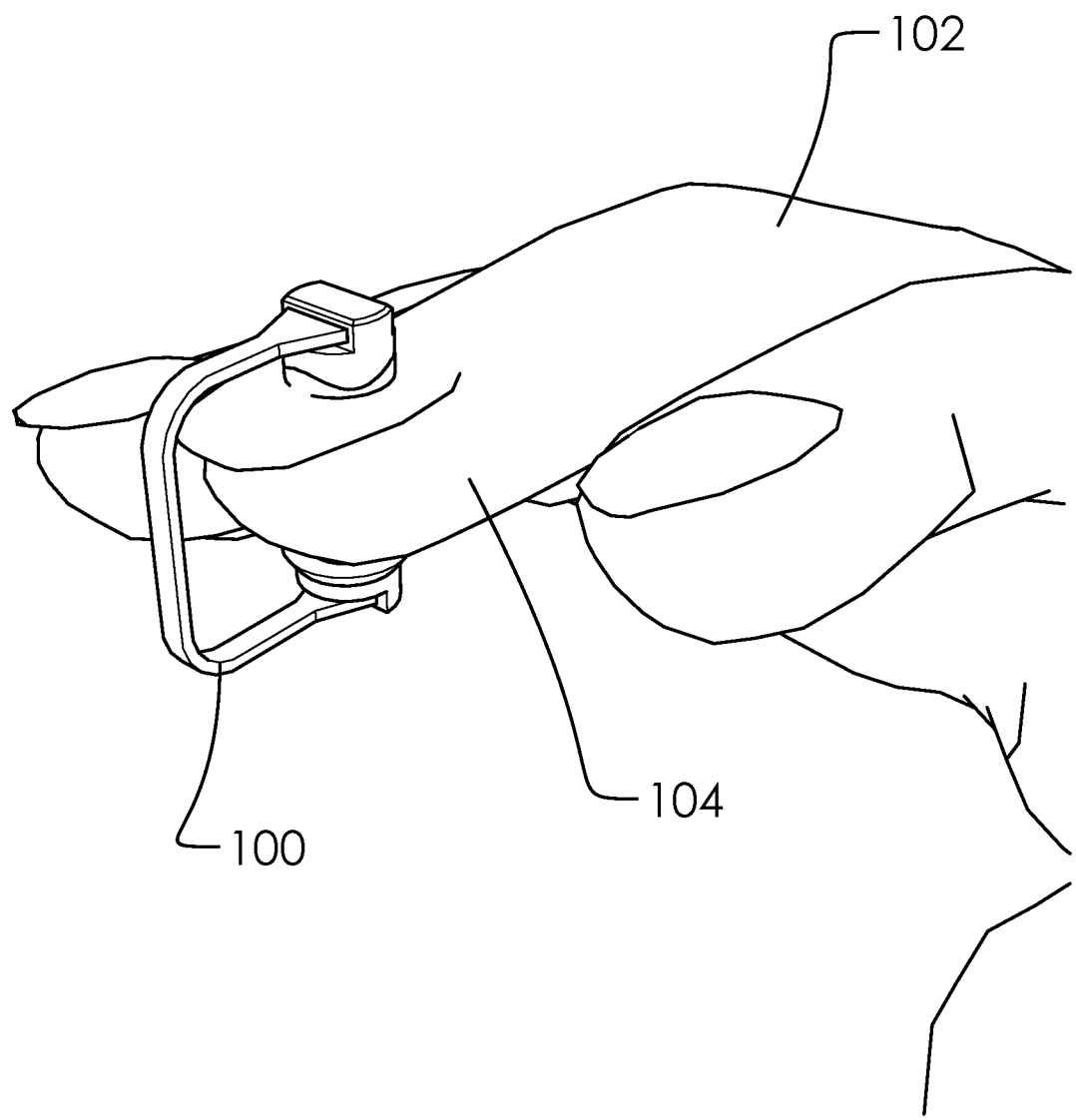
FIG. 1 illustrates a perspective overview view of a monitor system 100.

FIG. 1 illustrates a perspective overview view of a monitor system 100.

Said monitor system 100 can be configured to safely and securely attach to a hand 102 of a user, as discussed herein.

In one embodiment, said monitor system 100 can comprise a system for attaching a pulse sensor system to a finger 104 of a user.

When patients are hospitalized, they are often attached to pulse tracking systems such as pulse oximeters (PO) to monitor a person's oxygen saturation (SO2). PO's are configured to press a sensor against a thin part of a patient's skin, such as the fingertip. Thereafter, the PO will pass two wavelengths of light through the fingertip to a photo detector. The PO will thereafter measure/calculate changing absorbance of the wavelengths and thereby the absorbances due to pulsing arterial blood.

Typically, in the prior art, the PO will comprise a mechanism for holding the sensors and photo detector opposite one another; such as, a spring-loaded clamp and/or a tape.

Limits of PO includes "[erroneously] low readings may be caused by hypoperfusion of the extremity being used for monitoring (often due to a limb being cold, or from vasoconstriction secondary to the use of vasopressor agents); incorrect sensor application; highly calloused skin; or movement (such as shivering), especially during hypoperfusion.

To ensure accuracy, the sensor should return a steady pulse and/or pulse waveform." (https://en.wikipedia.org/wiki/Pulse_oximetry)

PO's are heavily used in this country. "According to a report by iData Research the U.S. pulse oximetry monitoring market for equipment and sensors was over 700 million USD in 2011." (U.S. Market for Patient Monitoring Equipment. iData Research. May 2012)

However, PO have fallen short for patients who must wear them for extended stays in the hospital. The use of tension/sprung clips and adhesive do not result in comfort to the patient. In fact, nurses will often tape the PO to the finger of the patient and leave it that way for days without changing the adhesive, the result of which is sick smelling skin due to moisture buildup and lack of air flow.

Said monitor system 100 can address these short comings and more of the prior art, as discussed herein.

Figure 2:
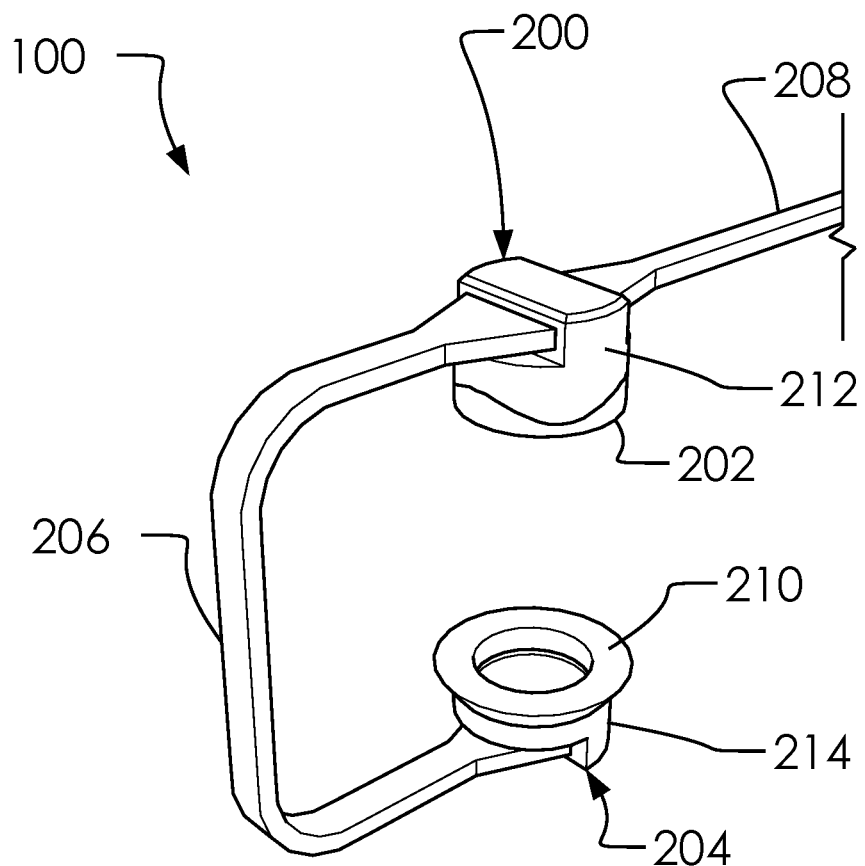
FIG. 2 illustrates a perspective overview view of said monitor system 100.

FIG. 2 illustrates a perspective overview view of said monitor system 100.

In one embodiment, an upper assembly 200 can comprise a cushion 210, a light emitter assembly 212 and a light receiver assembly 214.

In one embodiment, said monitor system 100 can comprise said upper assembly 200, a fixed portion 202, a lower assembly 204, an intermediate support 206 and a line 208.

Figure 3A:
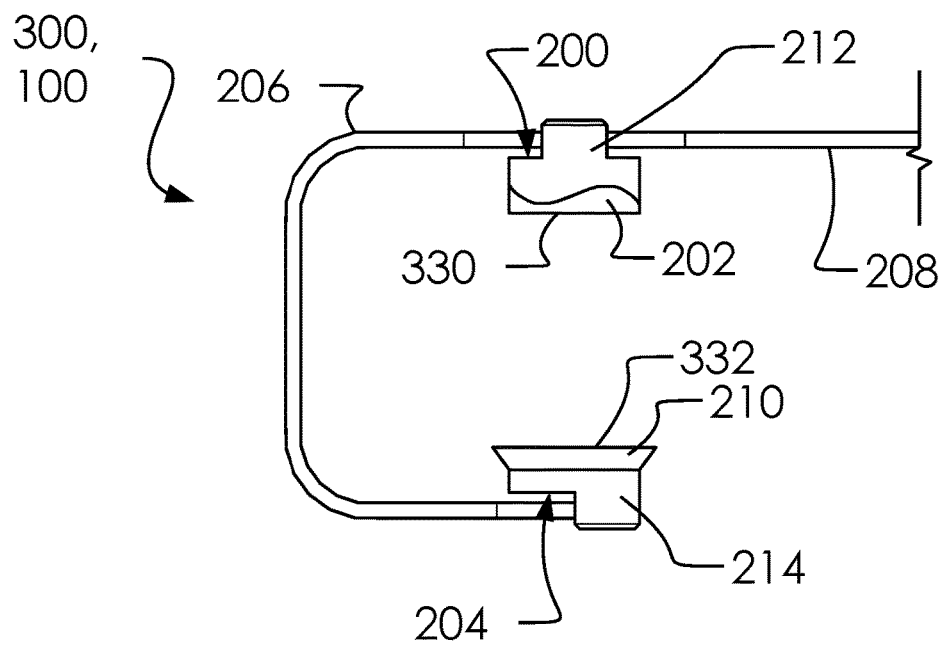
FIGS. 3A and 3B illustrate an elevated first side view of said monitor system 100.
Figure 3B:
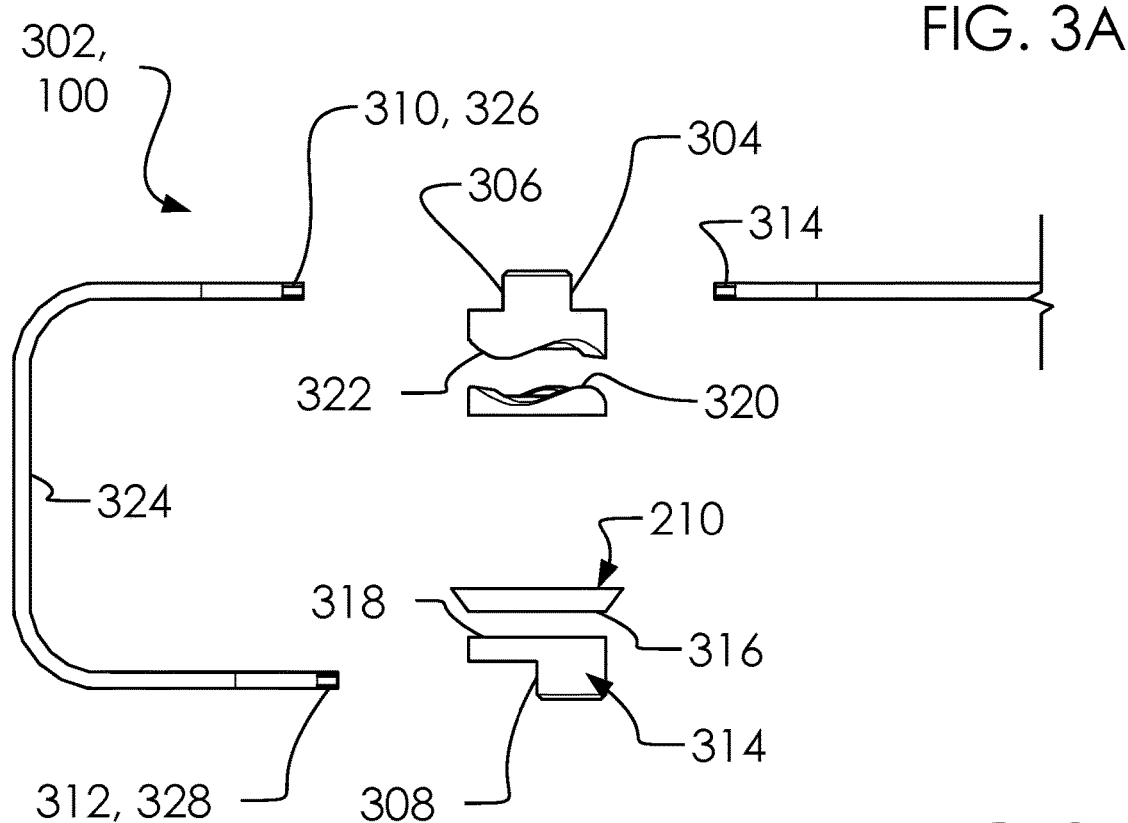

FIGS. 3A and 3B illustrate an elevated first side view of said monitor system 100.

In one embodiment, said monitor system 100 can comprise a closed configuration 300, an open configuration 302, a line socket 304, an intermediate upper socket 306 and an intermediate lower socket 308.

In one embodiment, said fixed portion 202 can comprise an upper surface 320 and an upper fingernail interface 330.

In one embodiment, said intermediate support 206 can comprise a first end 310, a second end 312, a line plug 314, a middle portion 324, a first end plug 326 and a second end plug 328.

In one embodiment, said light emitter assembly 212 can comprise a lower surface 322.

In one embodiment, said light receiver assembly 214 can comprise an upper surface 318.

In one embodiment, said cushion 210 can comprise a lower surface 316 and a lower finger interface 332.

In one embodiment, said monitor system 100 can comprise said upper assembly 200 attached to said lower assembly 204 with said intermediate support 206. In one embodiment, said intermediate support 206 can comprise a data communication line carrying information between said upper assembly 200 and said lower assembly 204. In one embodiment, said intermediate support 206 can comprise said first end 310 with said first end plug 326, said second end 312 with said second end plug 328, and said middle portion 324 between said ends.

In one embodiment, said first end plug 326 can plug into said upper assembly 200 and said second end plug 328 can plug into said lower assembly 204.

In one embodiment, said upper assembly 200 can comprise said light emitter assembly 212 and said fixed portion 202. In one embodiment, said upper assembly 200 can further comprise said intermediate upper socket 306 and said line socket 304; and said lower assembly 204 can comprise said intermediate lower socket 308. In one embodiment, said intermediate lower socket 308 can be in said light receiver assembly 214 and said intermediate upper socket 306 can be in said light emitter assembly 212. In one embodiment, said line socket 304 can selectively receive said line plug 314 of said line 208.

In one embodiment, said monitor system 100 can facilitate monitoring by passing power and data between said line 208, said intermediate support 206, said upper assembly 200 and said lower assembly 204. In one embodiment, said upper assembly 200 can emit light signals which are received and measured at said lower assembly 204.

Figure 4A:
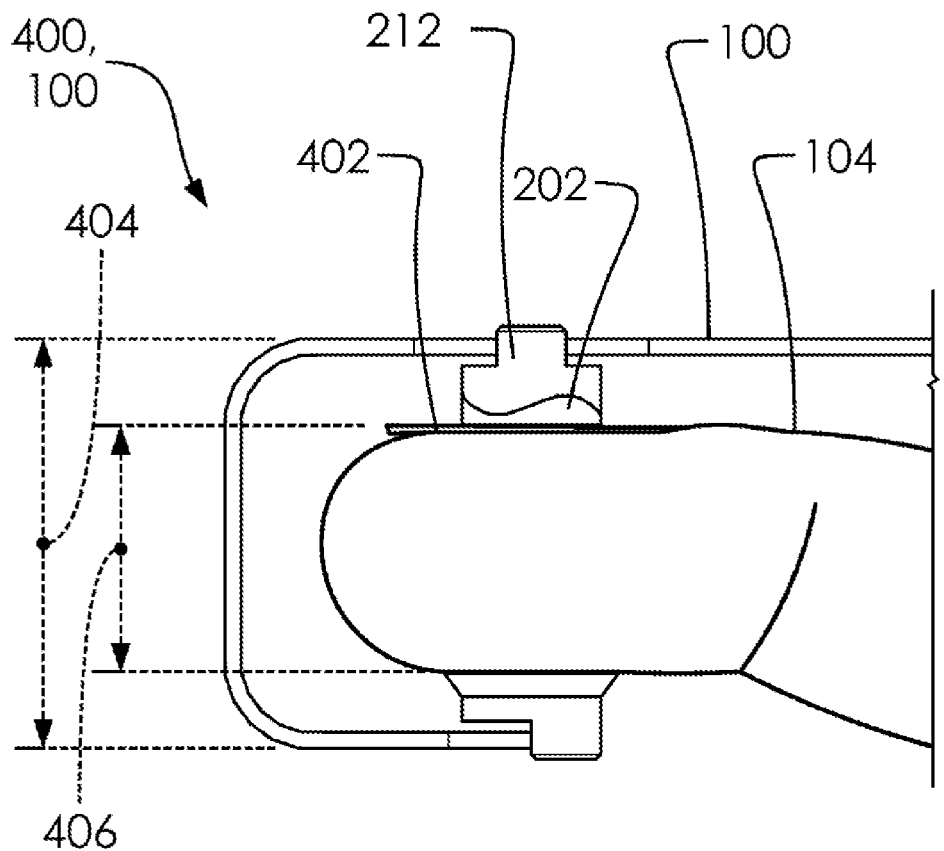
FIGS. 4A and 4B illustrate an elevated front side view of a first attached configuration 400, and detached configuration 408, respectively.
Figure 4B:
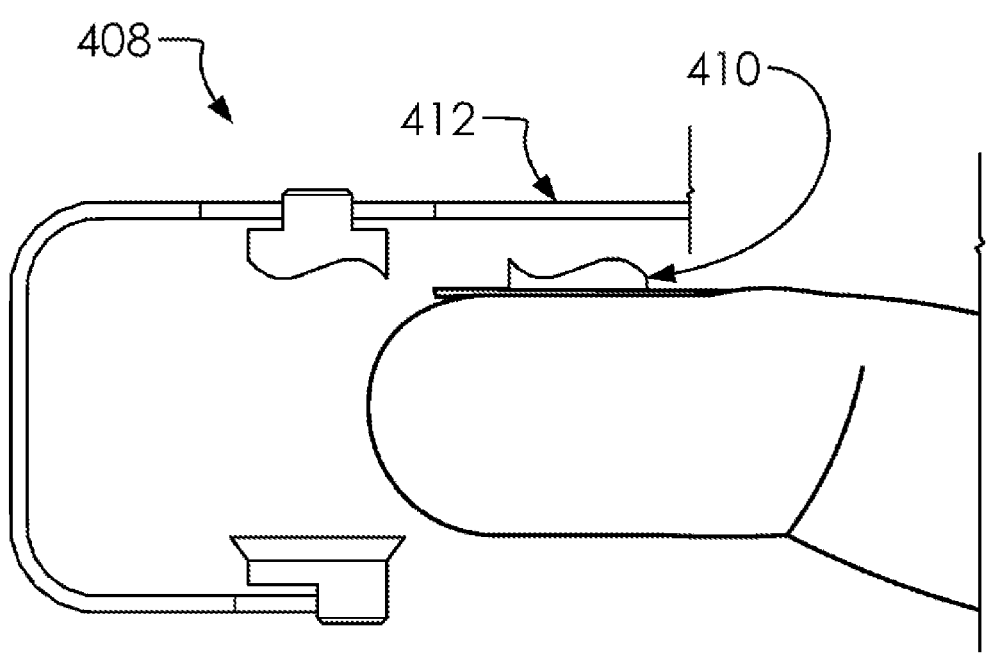

FIGS. 4A and 4B illustrate an elevated front side view of a first attached configuration 400, and detached configuration 408, respectively.

In one embodiment, said monitor system 100 can comprise said first attached configuration 400, a system height 404, said detached configuration 408, an attached portion 410 and a detached portion 412.

In one embodiment, said finger 104 can comprise a fingernail 402 and a finger height 406.

In one embodiment, said fixed portion 202 can be affixed to said fingernail 402 with an adhesive. In one embodiment, said adhesive can comprise a high bond material such as is used with synthetic cosmetic fingernails. In one embodiment, other parts of said monitor system 100 can detach from said fixed portion 202 so as to be moved or repositioned, as discussed herein.

In one embodiment, said light emitter assembly 212 and said fixed portion 202 can be magnetically or mechanically attached to one another.

In one embodiment, said system height 404 can be calibrated and adjusted to ensure said upper assembly 200 and said lower assembly 204 are aligned and squeezing a portion of said finger 104 for additionally attachment strength. Although not illustrated, said system height 404 can be variable with a telescoping or clipping element at said middle portion 324.

In one embodiment, said monitor system 100 can comprise said attached portion 410 and said detached portion 412. In one embodiment, said monitor system 100 can selectively attach to said finger 104 by attaching said attached portion 410 to said fingernail 402, and selectively attaching said detached portion 412 to said attached portion 410. In one embodiment, said detached portion 412 can comprise portions of said light emitter assembly 212, said monitor system 100, said lower assembly 204, and said middle portion 324.

Figure 5:
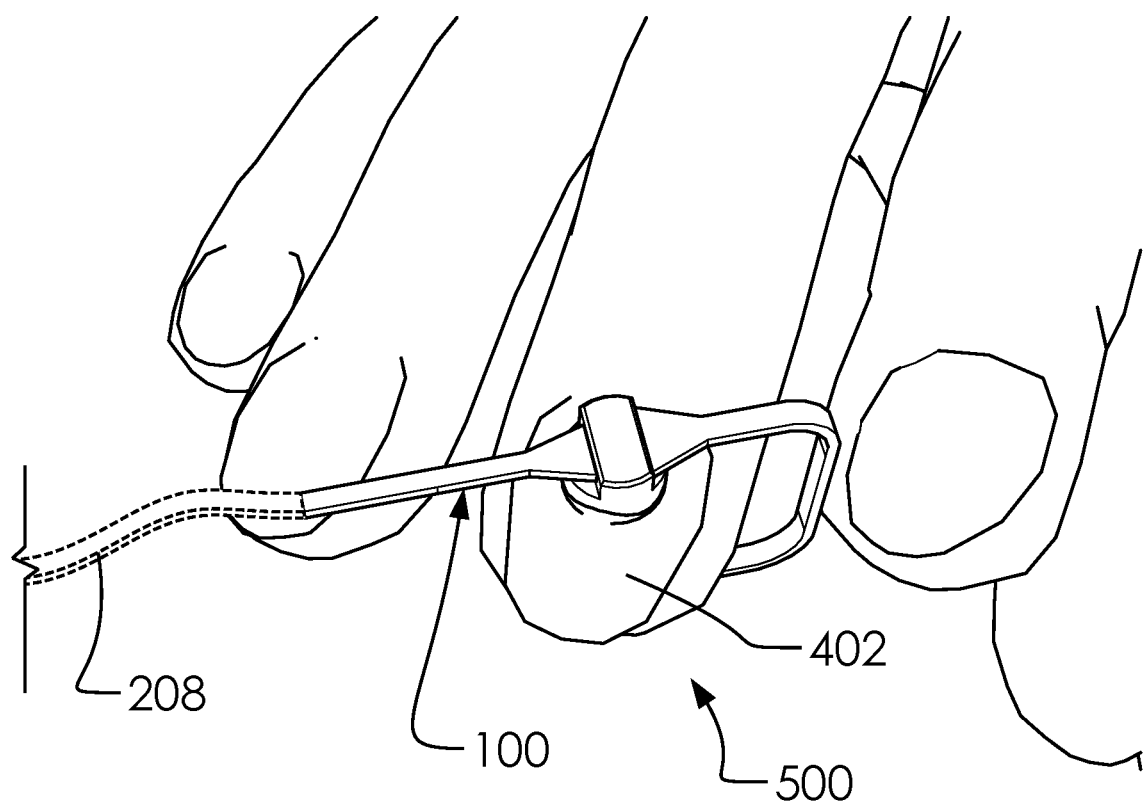
FIG. 5 illustrates a perspective overview view of said monitor system 100.

FIG. 5 illustrates a perspective overview view of said monitor system 100.

In one embodiment, said monitor system 100 can be rotated without adjusting said fixed portion 202, so as to move portions of said monitor system 100 for convenience, comfort or other needs of a patient.

Figure 6:
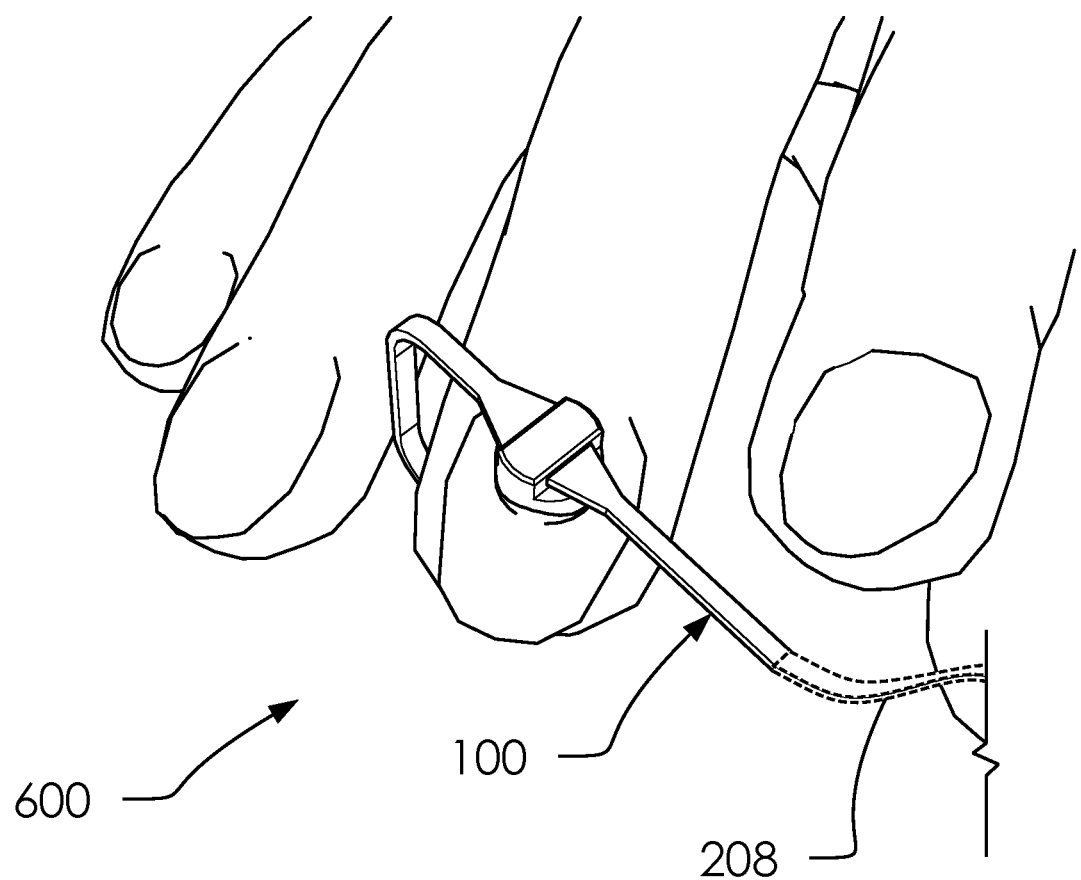
FIG. 6 illustrates a perspective overview view of a third attached configuration 600.

FIG. 6 illustrates a perspective overview view of a third attached configuration 600.

In one embodiment, said monitor system 100 can comprise a first concave portion 902a.

In one embodiment, said third attached configuration 600 can comprise said detached configuration 408 rotated 120 degrees counterclockwise from a second attached configuration 500.

Figure 7A:
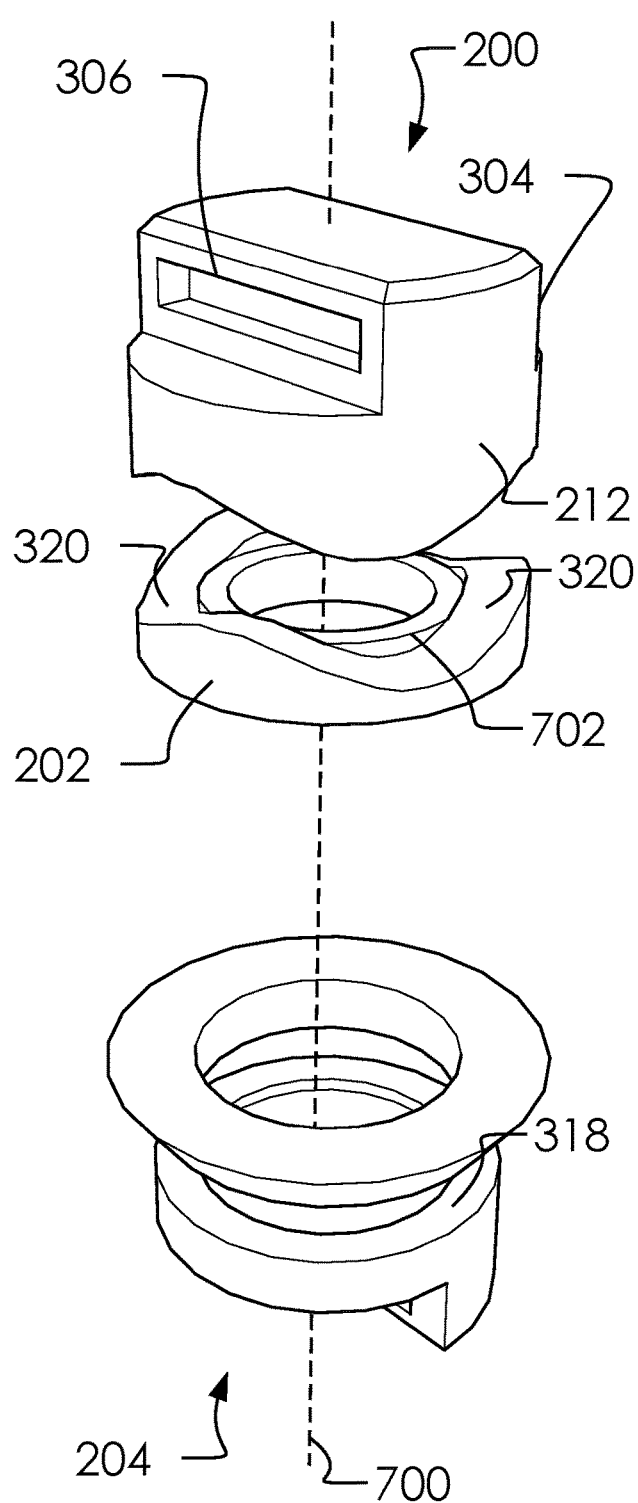
FIGS. 7A and 7B illustrate a perspective front side view of said monitor system 100.
Figure 7B:
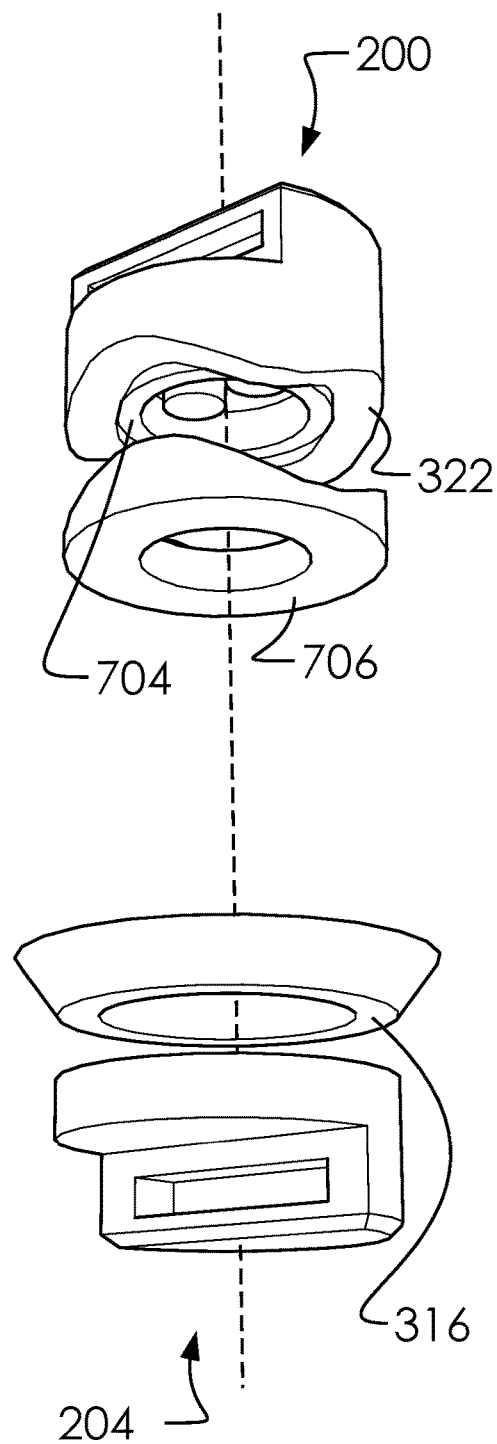

FIGS. 7A and 7B illustrate a perspective front side view of said monitor system 100.

In one embodiment, said monitor system 100 can comprise an alignment axis 700.

In one embodiment, said fixed portion 202 can comprise an affixed magnet 702 and a lower interface surface 706.

In one embodiment, said light emitter assembly 212 can comprise a detached magnet 704.

In one embodiment, said fixed portion 202 can comprise said affixed magnet 702 and said light emitter assembly 212 can comprise said detached magnet 704. In one embodiment, said detached magnet 704 and said affixed magnet 702 can selectively attach to one another.

In one embodiment, said detached magnet 704 can be within said light emitter assembly 212.

FIGS. 8A, 8B, 8C and 8D illustrate an exploded perspective front side view, a perspective bottom side view, an elevated front side view, and an elevated first side view of said upper assembly 200.

In one embodiment, an emitters 800 can be tucked within said light emitter assembly 212, as illustrated herein.

In one embodiment, said light emitter assembly 212 can comprise said emitters 800.

In one embodiment, said lower surface 322 can comprise said emitters 800.

Figure 9A:
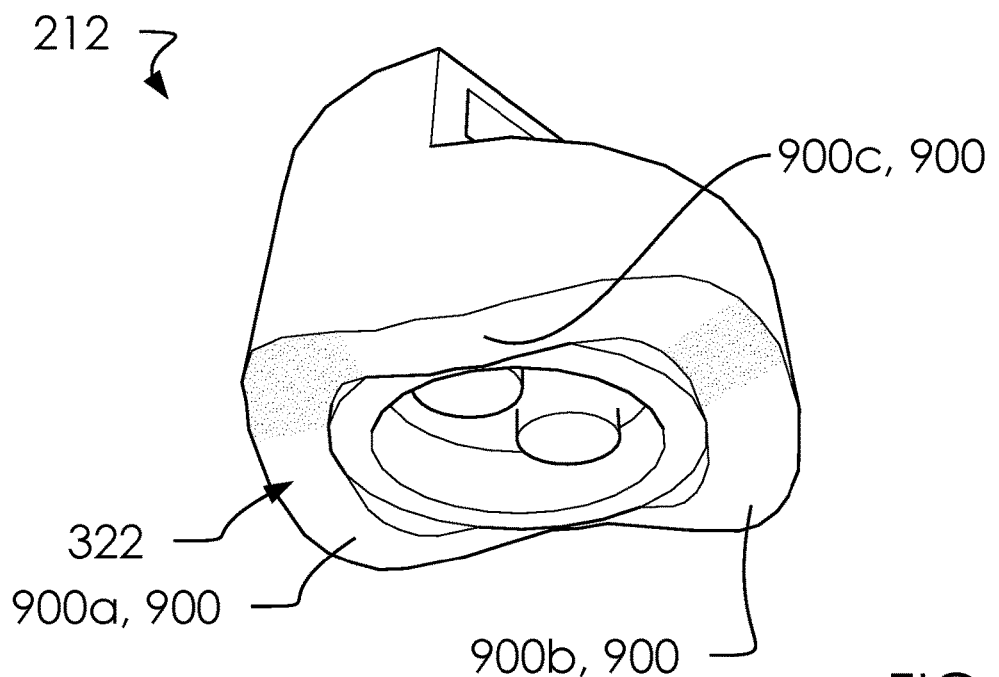
FIGS. 9A and 9B illustrate a perspective bottom side view of a light emitter assembly 212.
Figure 9B:
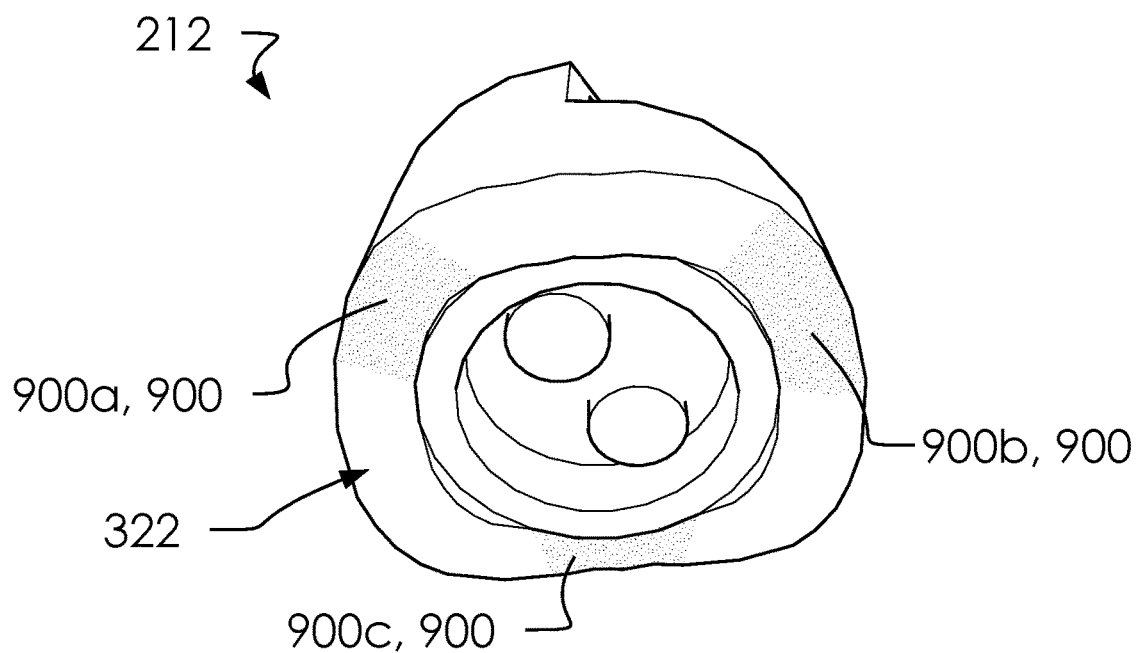
Figure 10A:
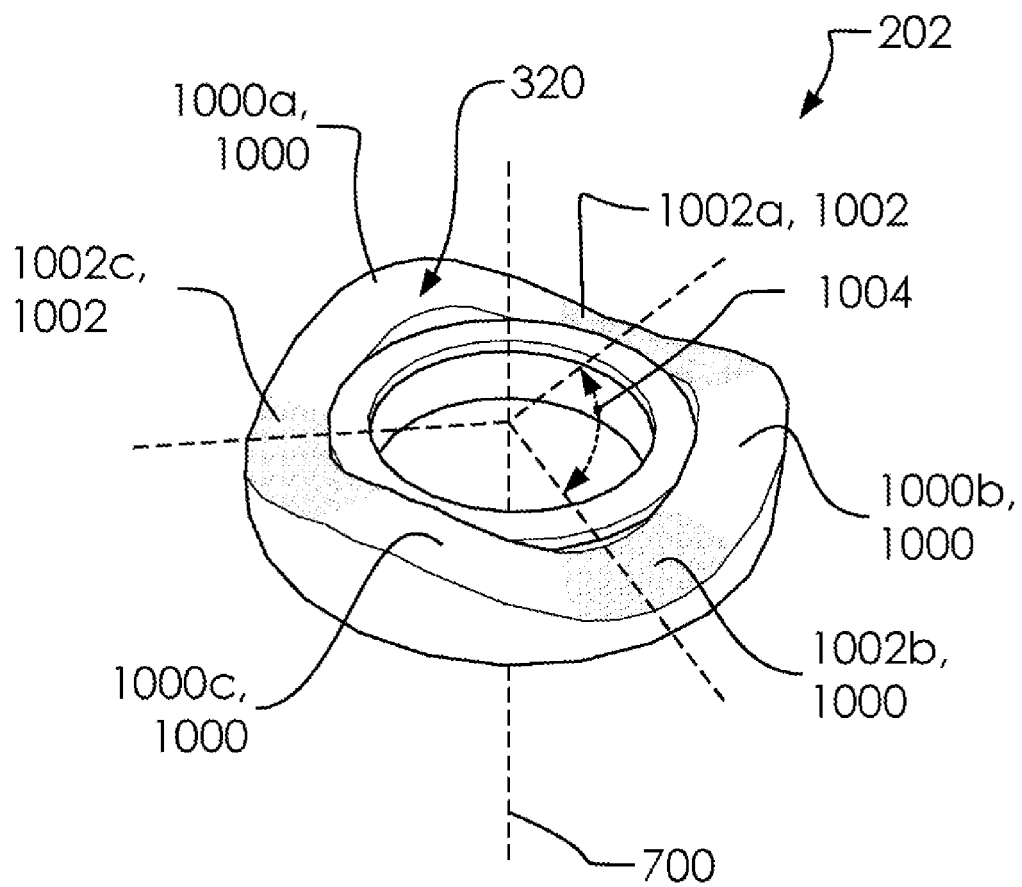
FIGS. 10A, 10B, 10C and 10D illustrate a perspective overview, bottom side view, front side and first side view of a fixed portion 202.
Figure 10B:
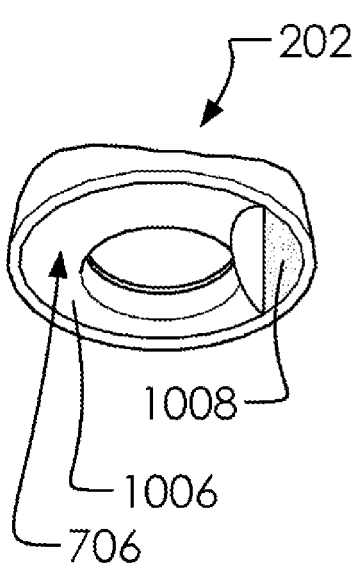
Figure 10C:
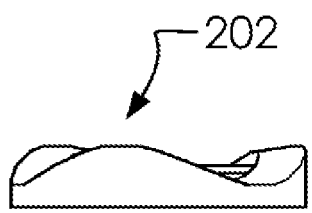
Figure 10D:
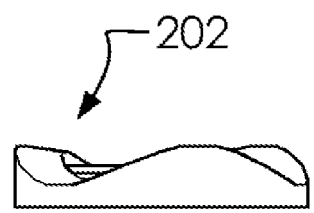

FIGS. 9A and 9B illustrate a perspective bottom side view of said light emitter assembly 212.

In one embodiment, one or more convex portions 900 can comprise a first convex portion 900*a*, a second convex portion 900*b* and a third convex portion 900*c*.

In one embodiment, one or more concave portions 902 can comprise said first concave portion 902*a*, a second concave portion 902*b* and third concave portion 902*c*.

Said fixed portion 202 and said light emitter assembly 212 can comprise said upper surface 320 and said lower surface 322, which respectively mate into one another. Each among said upper surface 320 and said lower surface 322 can comprise a substantially round element having a wave shaped cut oscillating between said one or more convex portions 900 and said one or more concave portions 902. Accordingly, said one or more convex portions 900 of said upper surface 320 can nest within said one or more concave portions 902 of said lower surface 322; and vis versa.

In one embodiment, said fixed portion 202 can said third concave portion 902*c*.

In one embodiment, said upper surface 320 comprise said third concave portion 902*c*.

In one embodiment, said lower surface 322 can comprise said one or more convex portions 900, and said one or more concave portions 902.

In one embodiment, said lower surface 322 can be divided up into groupings of said one or more convex portions 900 and said one or more concave portions 902, in alternating patterns, as illustrated.

FIGS. 10A, 10B, 10C and 10D illustrate a perspective overview, bottom side view, front side and first side view of said fixed portion 202.

In one embodiment, one or more concave portions 1000 can comprise a first concave portion 1000*a*, a second concave portion 1000*b* and a third concave portion 1000*c*.

In one embodiment, one or more convex portions 1002 can comprise a first convex portion 1002*a*, a second convex portion 1002*b*, a third convex portion 1002*c* and a radial separation 1004.

In one embodiment, said upper surface 320 can comprise said one or more concave portions 1000, said third concave portion 1000*c* and said one or more convex portions 1002.

In one embodiment, said lower interface surface 706 can comprise an adhesive cover 1006 and an adhesive layer 1008.

In one embodiment, said upper surface 320 of said fixed portion 202 can comprise said one or more concave portions 1000 and said one or more convex portions 1002 in an alternating pattern, as illustrated. Said one or more convex portions 1002 can be separated by said radial separation 1004. In one embodiment, said radial separation 1004 can comprise 120 degrees.

In one embodiment, said one or more concave portions 1000 can selectively fit within said one or more concave portions 902 and said one or more convex portions 1002 can selectively fit within said one or more convex portions 900.

In one embodiment, said lower interface surface 706 can be configured to selectively attach to said fingernail 402. In one embodiment, selectively attaching said lower interface surface 706 to said fingernail 402 can comprise removing said adhesive cover 1006 and applying said adhesive layer 1008 against said fingernail 402.

In one embodiment, said adhesive layer 1008 can be like adhesives used for press on fingernails, as is known in the art.

Figure 11A:
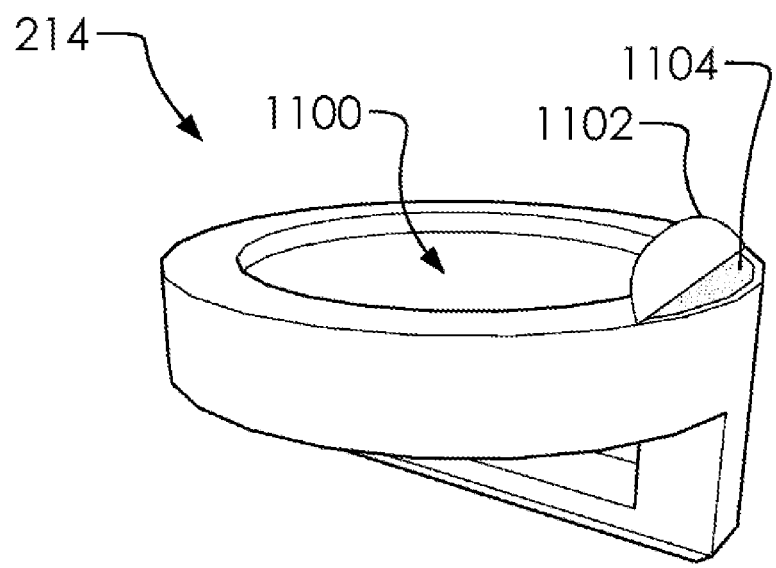
FIGS. 11A, 11B and 11C illustrate a perspective overview, an elevated front and first side view of a light receiver assembly 214.
Figure 11B:
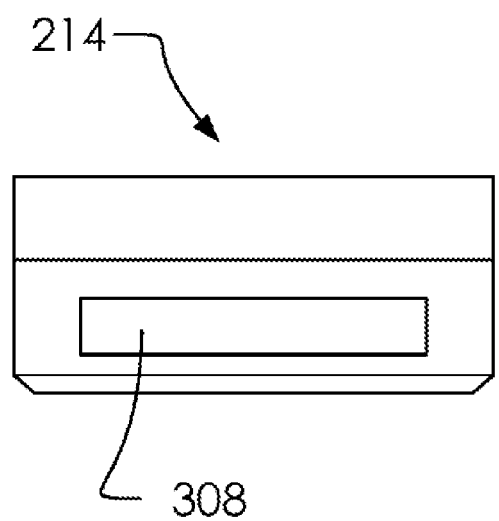
Figure 11C:
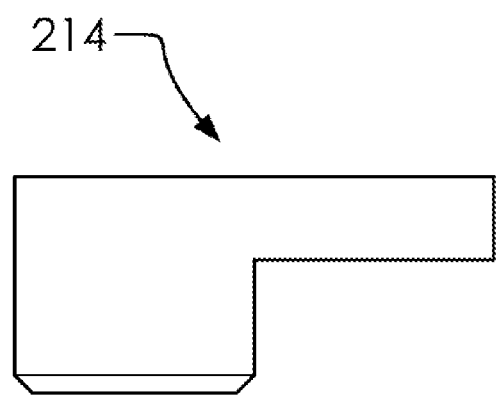

FIGS. 11A, 11B and 11C illustrate a perspective overview, an elevated front and first side view of said light receiver assembly 214.

In one embodiment, said light receiver assembly 214 can comprise light receiver sensor 1100, an adhesive cover 1102, and an adhesive layer 1104.

In one embodiment, said light receiver sensor 1100 can be configured to receive signals from said emitters 800, as is known in the art.

In one embodiment, said adhesive layer 1104 can be selectively exposed and pressed against a portion of said cushion 210.

Figures 12A, 12B:
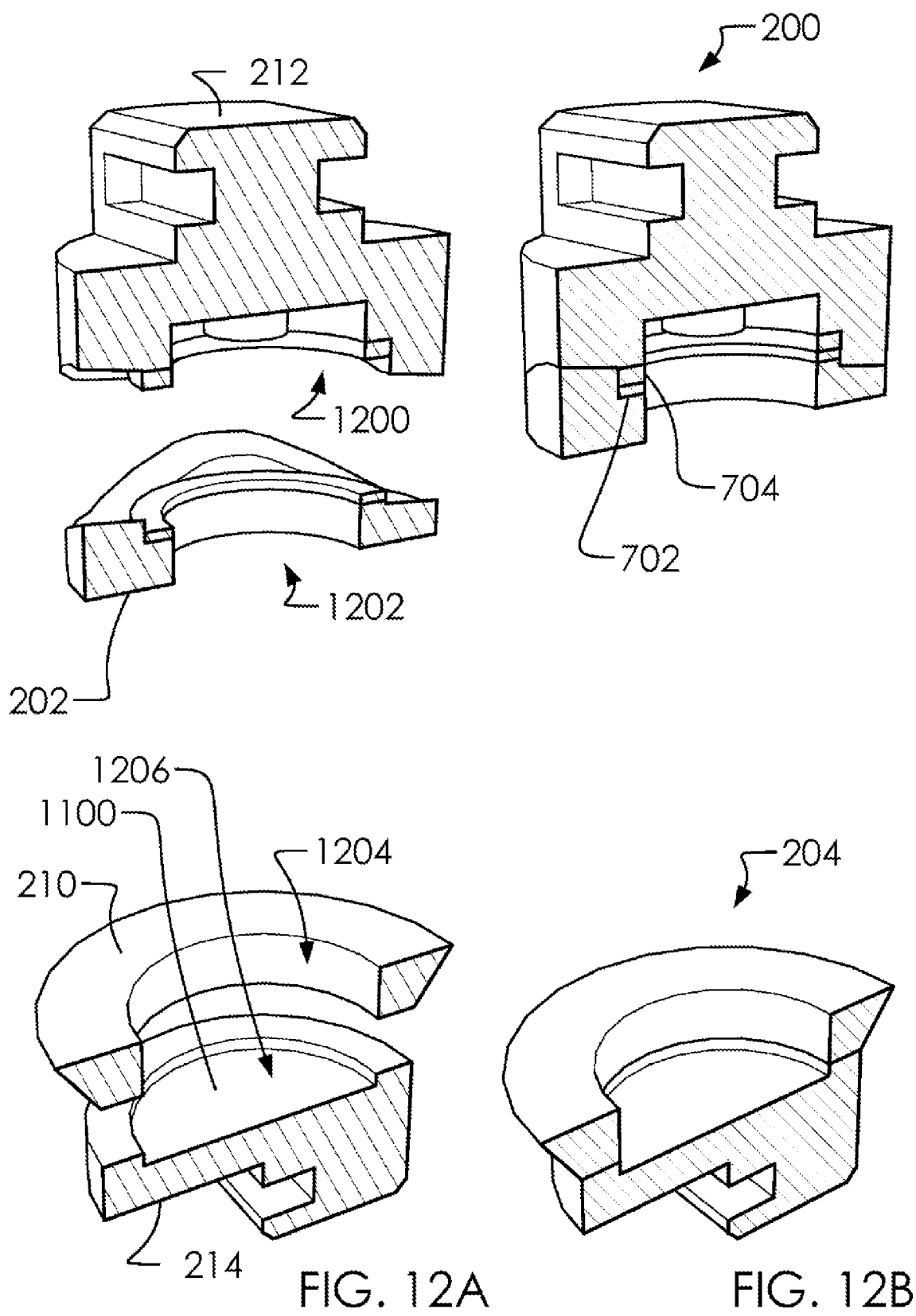
FIGS. 12A and 12B illustrate a perspective overview view of said upper assembly 200.

FIGS. 12A and 12B illustrate a perspective overview view of said upper assembly 200.

In one embodiment, said fixed portion 202 can comprise an aperture 1202.

In one embodiment, said light emitter assembly 212 can comprise a lower aperture 1200.

In one embodiment, said light receiver assembly 214 can comprise a sensor aperture 1206.

In one embodiment, said cushion 210 can comprise an aperture 1204.

In one embodiment, said lower aperture 1200, said aperture 1202, said aperture 1204, and said sensor aperture 1206 can be aligned on said alignment axis 700.

As shown in FIG. 12B, said detached magnet 704 and said affixed magnet 702 can be aligned and selectively attached to one another with said upper assembly 200 in an attached configuration.

Concerning the cross-section rendering, said upper assembly 200 and said lower assembly 204 do not show electrical components or cavities within its elements. In an real world configuration, each of these may have electrical elements and cavities, as is known in the art. Additionally, said line socket 304, said intermediate upper socket 306 and said intermediate lower socket 308 may have plugs for pairing with said first end 310, said line plug 314 and said second end 312, as is known in the art.

Figure 13:
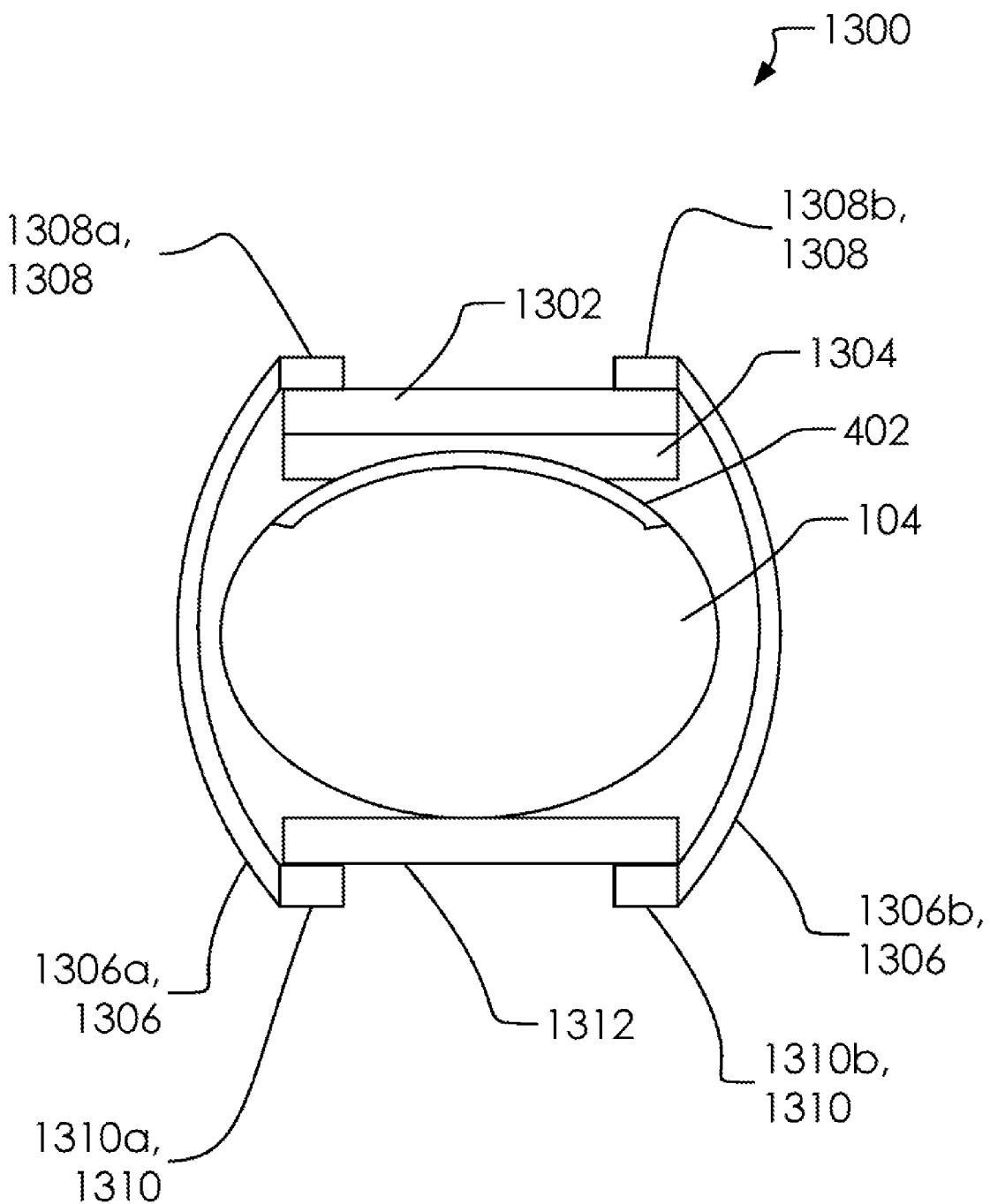
FIG. 13 illustrates an elevated first side view of a side clamp monitoring system 1300.

FIG. 13 illustrates an elevated first side view of a side clamp monitoring system 1300.

In one embodiment, said side clamp monitoring system 1300 can comprise a communication hardware 1502, a power system 1506, an input-output ports 1504, a sensors 1508

In one embodiment, one or more side portions 1306 can comprise a first side portion 1306*a* and a second side portion 1306*b*.

In one embodiment, one or more upper notches 1308 can comprise a first upper notch 1308*a* and second upper notch 1308*b*.

In one embodiment, one or more lower notches 1310 can comprise a first lower notch 1310*a* and a second lower notch 1310*b*.

In one embodiment, said side clamp monitoring system 1300 can comprise a light emitter assembly 1302, a fixed portion 1304, said one or more side portions 1306, said one or more upper notches 1308, said one or more lower notches 1310 and a light receiver assembly 1312.

In one embodiment, said side clamp monitoring system 1300 can comprise an alternative embodiment of said monitor system 100. Wherein, said upper assembly 200 and said lower assembly 204 are attached to one another with said one or more side portions 1306 rather than said intermediate support 206.

In one embodiment, said side clamp monitoring system 1300 can be in a fixed orientation with respect to said finger 104.

In one embodiment, components of said side clamp monitoring system 1300 can function substantially identical to that of said monitor system 100, where named the same name.

In one embodiment, said fixed portion 1304 can comprise said detached portion 412 and the other elements can comprise said attached portion 410.

In one embodiment, said one or more upper notches 1308 and/or said one or more lower notches 1310 can detach or selectively attached between said light emitter assembly 1302 and said light receiver assembly 1312.

In one embodiment, data can be passed between said light emitter assembly 1302 and said light receiver assembly 1312 through one or both of said one or more side portions 1306.

In one embodiment, said one or more side portions 1306 and/or said intermediate support 206 can comprise variable lengths to more firmly wrap around portions of said finger 104.

Said side clamp monitoring system 1300 is illustrated without said line 208 for simplicity, but said side clamp monitoring system 1300 may include said line 208 (or similar).

In one embodiment, said side clamp monitoring system 1300 and/or said monitor system 100 can operate wirelessly, as is known in the art.

Figure 14:
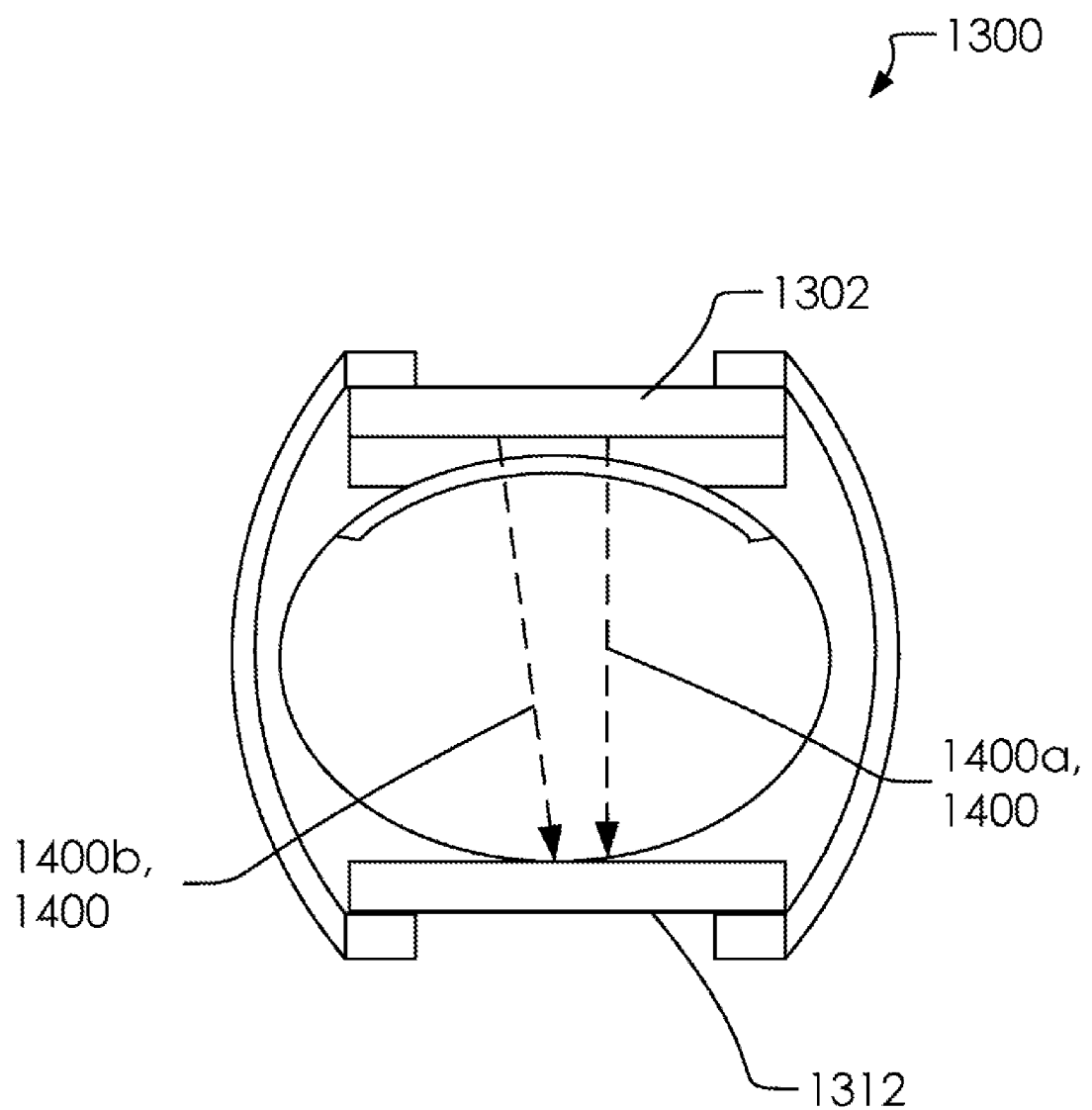
FIG. 14 illustrates an elevated front side view of said side clamp monitoring system 1300.

FIG. 14 illustrates an elevated front side view of said side clamp monitoring system 1300.

In one embodiment, said side clamp monitoring system 1300 can comprise one or more emitted lights 1400.

In one embodiment, said monitor system 100 can comprise said one or more emitted lights 1400.

In one embodiment, said one or more emitted lights 1400 can comprise a first emitted light 1400*a* and a second emitted light 1400*b*.

In one embodiment, a portion of said light emitter assembly 1302 can transmit said one or more emitted lights 1400 through a portion of said finger 104 and a portion of said light receiver assembly 1312 can receive those light signals.

Figures 15A, 15B:
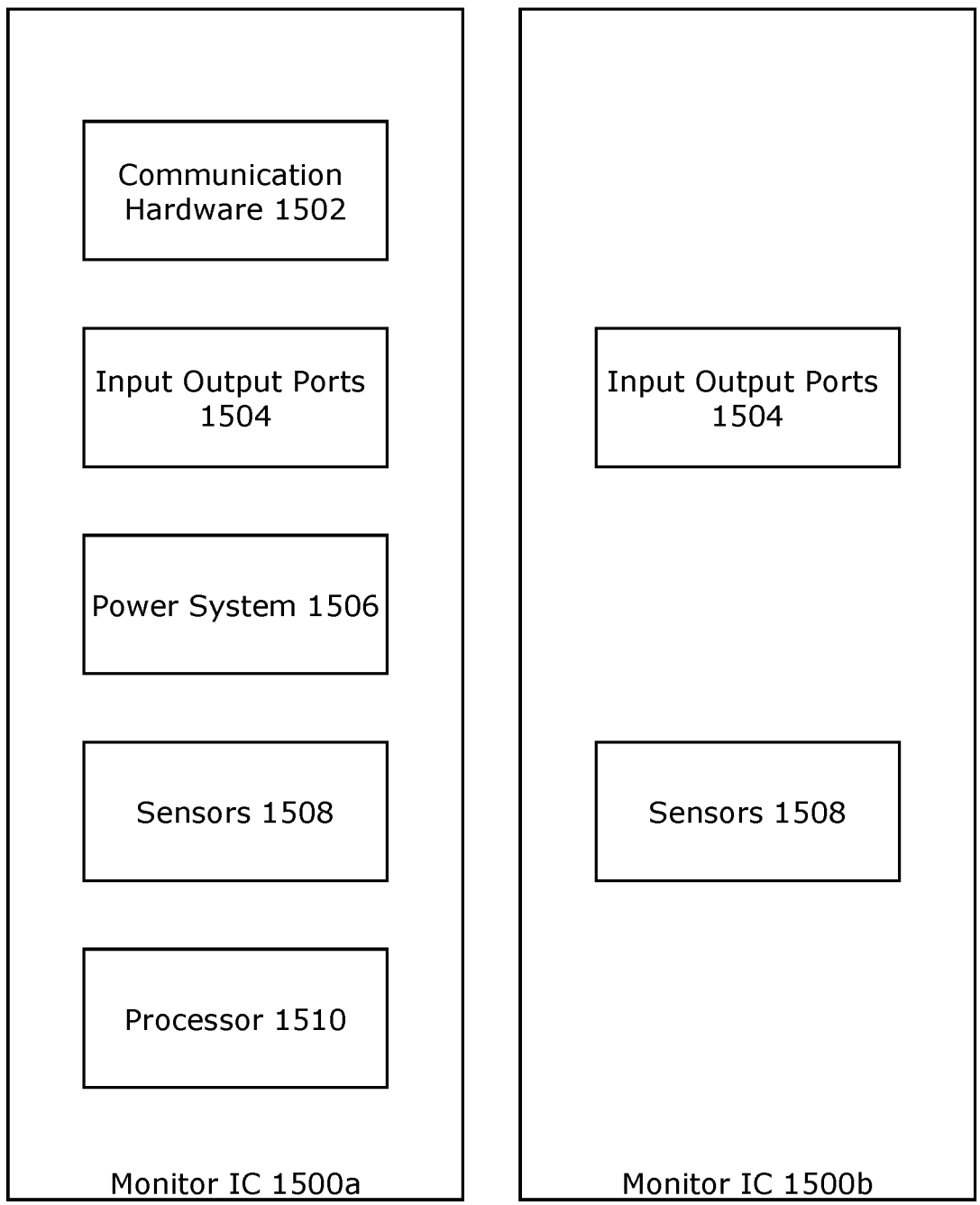
FIGS. 15A and 15B illustrate a view of a first Monitor IC 1500a, and a second Monitor IC 1500b, respectively.

FIGS. 15A and 15B illustrate a view of a first Monitor IC 1500*a*, and a second Monitor IC 1500*b*, respectively.

In one embodiment, said monitor system 100 can comprise said first Monitor IC 1500*a* and/or said second Monitor IC 1500*b* (collectively referred to as a Monitor Ics 1500).

In one embodiment, said Monitor Ics 1500 can comprise said first Monitor IC 1500*a*, said second Monitor IC 1500*b*, said communication hardware 1502, said input-output ports 1504, said power system 1506, said sensors 1508 and one or more processors 1510

In one embodiment, said first Monitor IC 1500*a* can comprise a wireless configuration of said monitor system 100. In one embodiment, said monitor system 100 can comprise just said input-output ports 1504 and said sensors 1508, wherein signals generated and collected are passed back through said line 208 to existing monitoring systems.

Said Monitor Ics 1500 can comprise an integrated system with processing and power integrated. Said communication hardware 1502 can be used to communicate signals from said monitor system 100 to existing medical equipment, as is known in the art.

Figure 16:
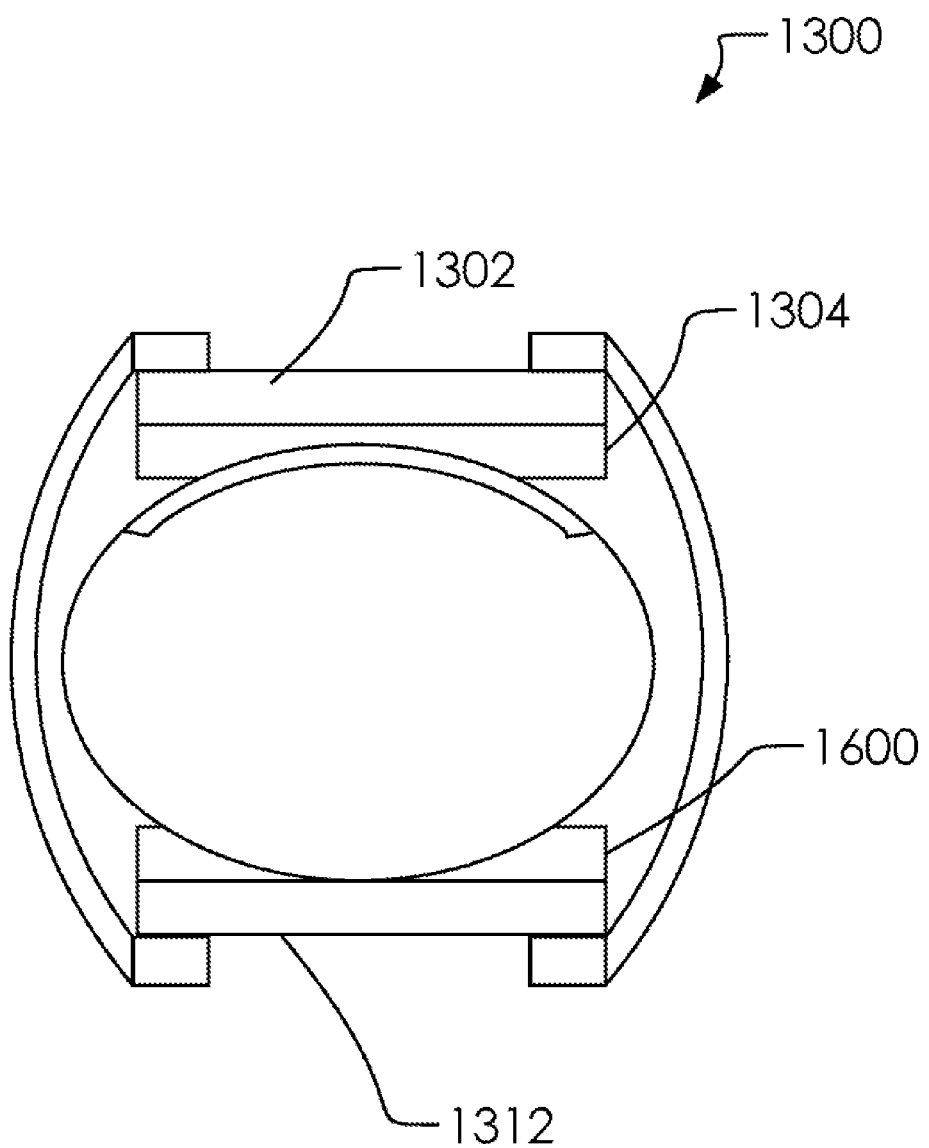
FIG. 16 illustrates an elevated front side view of said side clamp monitoring system 1300.

FIG. 16 illustrates an elevated front side view of said side clamp monitoring system 1300.

In one embodiment, said side clamp monitoring system 1300 can comprise a cushion 1600.

In one embodiment, said side clamp monitoring system 1300 can comprise said cushion 1600, similar to said cushion 210 of said monitor system 100.

The following sentences are included for completeness of this disclosure with reference to the claims.

Said monitor system 100 configured to selectively attach said light emitter assembly 212 and said light receiver assembly 214 to said finger 104. Said monitor system 100 comprising said light emitter assembly 212, said light receiver assembly 214, said upper assembly 200 said lower assembly 204, and said intermediate support 206. Said monitor system 100 comprises said attached portion 410 and said detached portion 412. Said attached portion 410 can be configured to attach to said fingernail 402 of said finger 104. Said detached portion 412 can be configured to selectively and releasably attach to said attached portion 410. Said monitor system 100 can be configured to emit said one or more emitted lights 1400 through said finger 104 between said light emitter assembly 212 and said light receiver assembly 214.

Said system height 404 can be configured to be calibrated and adjusted to ensure said upper assembly 200 and said lower assembly 204 can be aligned by squeezing a portion of said finger 104 for additionally attachment strength.

Said monitor system 100 facilitates monitoring by passing power and data between said line 208, said intermediate support 206, said upper assembly 200 and said lower assembly 204.

Said upper assembly 200 emits light signals which can be received and measured at said lower assembly 204.

Said upper assembly 200 comprises said light emitter assembly 212 and said fixed portion 202. Said upper assembly 200 further comprises said intermediate upper socket 306 and said line socket 304. Said lower assembly 204 comprises said intermediate lower socket 308. Said intermediate lower socket 308 can be in said light receiver assembly 214 and said intermediate upper socket 306 can be in said light emitter assembly 212.

Said light receiver assembly 214 comprises said light receiver sensor 1100. Said light receiver sensor 1100 can be configured to receive signals from said emitters 800.

Said lower assembly 204 further comprises said cushion 210. Said cushion 210 comprises said aperture 1204. Said cushion 210 and said light receiver assembly 214 can be attached to one another with said adhesive layer 1104.

Said fixed portion 202 further comprises said lower interface surface 706 comprising said adhesive cover 1006 and said adhesive layer 1008. Said lower interface surface 706 can be configured to selectively attach to said fingernail 402 by removing said adhesive cover 1006 and applying said adhesive layer 1008 against said fingernail 402.

Said light emitter assembly 212 comprises said lower surface 322, and said fixed portion 202 comprises said upper surface 320. Said upper surface 320 of said fixed portion 202 and said lower surface 322 of said light emitter assembly 212 mate into one another.

each among said upper surface 320 and said lower surface 322 can be a substantially round element having a wave shaped cut oscillating between said one or more convex portions 900 and said one or more concave portions 902. Said one or more convex portions 900 of said upper surface 320 nest within said one or more concave portions 902 of said lower surface 322. vis versa.

Said one or more concave portions 1000 comprise said first concave portion 1000a, said second concave portion 1000b and said third concave portion 1000c. Said one or more convex portions 1002 comprise said first convex portion 1002a, said second convex portion 1002b, said third convex portion 1002c. Said one or more convex portions 1002 can be separated by said radial separation 1004.

Said monitor system 100 can be configured to be rotated without adjusting said fixed portion 202, to move portions of said monitor system 100 for convenience, comfort or other needs of a patient.

Said line socket 304 selectively receives said line plug 314 of said line 208.

Said intermediate support 206 comprises said first end 310 with said first end plug 326, said second end 312 with said second end plug 328, and said middle portion 324 between said ends. Said first end plug 326 plugs into said upper assembly 200 and said second end plug 328 plugs into said lower assembly 204.

Said upper assembly 200 can be attached to said lower assembly 204 with said intermediate support 206. Said intermediate support 206 comprises a data communication line carrying information between said upper assembly 200 and said lower assembly 204.

Said fixed portion 202 can be affixed to said fingernail 402 with an adhesive. said adhesive comprises a high bond material such as can be used with synthetic cosmetic fingernails. other parts of said monitor system 100 can be configured to detach from said fixed portion 202 so as to be moved or repositioned.

Said light emitter assembly 212 and said fixed portion 202 can be magnetically or mechanically attached to one another.

Said monitor system 100 comprises said attached portion 410 and said detached portion 412. Said monitor system 100 can be configured to selectively attach to said finger 104 by attaching said attached portion 410 to said fingernail 402, and selectively attaching said detached portion 412 to said attached portion 410. Said detached portion 412 comprises portions of said light emitter assembly 212, said monitor system 100, said lower assembly 204, and said middle portion 324.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A monitor system configured to selectively attach a light emitter assembly and a light receiver assembly to a finger, wherein:
   said monitor system comprising said light emitter assembly, said light receiver assembly, an upper assembly, a lower assembly, and an intermediate support;
   said upper assembly comprises said light emitter, a fixed portion, and a detached portion;
   said fixed portion is configured to attach to a fingernail of said finger;
   said detached portion is configured to selectively and releasably attach to said fixed portion;
   said monitor system is configured to emit one or more emitted lights through said finger between said light emitter assembly and said light receiver assembly;
   said upper assembly further comprises an intermediate upper socket and a line socket; and
   said lower assembly comprises an intermediate lower socket; and
   said intermediate lower socket is in said light receiver assembly and said intermediate upper socket is in said light emitter assembly.

2. The monitor system of claim 1, wherein:
   a system height is configured to be adjusted to ensure said upper assembly and said lower assembly are aligned.

3. The monitor system of claim 1, wherein:
   said monitor system facilitates monitoring by passing power and data between a line,
   said intermediate support, said upper assembly and said lower assembly.

4. The monitor system of claim 1, wherein:
   said light receiver assembly comprises a light receiver sensor; and
   said light receiver sensor is configured to receive signals from an emitter.

5. The monitor system of claim 4, wherein:
   said lower assembly further comprises a cushion;
   said cushion comprises an aperture; and
   said cushion and said light receiver assembly are attached to one another with an adhesive layer.

6. The monitor system of claim 1, wherein:
   said fixed portion further comprises a lower interface surface comprising an adhesive cover and an adhesive layer;
   said lower interface surface is configured to selectively attach to said fingernail by
   removing said adhesive cover and
   applying said adhesive layer against said fingernail.

7. The monitor system of claim 1, wherein:
   said light emitter assembly comprises a lower surface, and said fixed portion comprises an upper surface; and
   said upper surface of said fixed portion and said lower surface of said light emitter assembly mate into one another.

8. The monitor system of claim 7, wherein:
   each among said upper surface and said lower surface are a substantially round element having a wave shaped cut oscillating between one or more convex portions and one or more concave portions; and
   said one or more convex portions of said upper surface nest within said one or more concave portions of said lower surface.

9. The monitor system of claim 8, wherein:
   one or more concave portions comprise a first concave portion, a second concave portion and a third concave portion;

one or more convex portions comprise a first convex portion, a second convex portion, a third convex portion; and said one or more convex portions are separated by a radial separation.

10. The monitor system of claim 1, wherein:

said intermediate support comprises a first end with a first end plug, a second end with a second end plug, and a middle portion between said ends; and said first end plug plugs into said upper assembly and said second end plug plugs into said lower assembly.

11. The monitor system of claim 1, wherein:

said upper assembly is attached to said lower assembly with said intermediate support; and said intermediate support comprises a data communication line carrying information between said upper assembly and said lower assembly.

12. The monitor system of claim 1, wherein:

said fixed portion is affixed to said fingernail with an adhesive;

said adhesive comprises a high bond material such as is used with synthetic cosmetic fingernails; and other parts of said monitor system are configured to detach from said fixed portion so as to be moved or repositioned.

13. The monitor system of claim 1, wherein:

said light emitter assembly and said fixed portion is magnetically or mechanically attached to one another.

* * * * *